US010422790B2

(12) United States Patent
Yoshida et al.

(10) Patent No.: US 10,422,790 B2
(45) Date of Patent: Sep. 24, 2019

(54) IMMUNOCHROMATOGRAPHIC TEST STRIP AND DETECTION METHOD USING IMMUNOCHROMATOGRAPHY FOR DETECTING TARGET IN RED BLOOD CELL-CONTAINING SAMPLE

(71) Applicant: SEKISUI MEDICAL CO., LTD., Tokyo (JP)

(72) Inventors: Mayumi Yoshida, Tokyo (JP); Mitsuaki Yamamoto, Tokyo (JP); Shinya Yokokawa, Tokyo (JP); Tomo Shimizu, Tokyo (JP); Keigo Kono, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 83 days.

(21) Appl. No.: 15/853,503

(22) Filed: Dec. 22, 2017

(65) Prior Publication Data

US 2018/0120303 A1 May 3, 2018

Related U.S. Application Data

(62) Division of application No. 14/389,180, filed as application No. PCT/JP2013/060003 on Apr. 1, 2013, now Pat. No. 9,885,707.

(30) Foreign Application Priority Data

Mar. 30, 2012 (JP) ................................ 2012-083165

(51) Int. Cl.
*G01N 33/558* (2006.01)
*G01N 33/53* (2006.01)
(Continued)

(52) U.S. Cl.
CPC ..... *G01N 33/5306* (2013.01); *G01N 33/5005* (2013.01); *G01N 33/54366* (2013.01);
(Continued)

(58) Field of Classification Search
None
See application file for complete search history.

(56) References Cited

U.S. PATENT DOCUMENTS 4,594,327 A 6/1986 Zuk
4,933,092 A 6/1990 Aunet et al.
(Continued)

FOREIGN PATENT DOCUMENTS

EP 0 271 204 A2 6/1988
EP 2 833 145 A1 2/2015
(Continued)

OTHER PUBLICATIONS

English translation of International Preliminary Report on Patentability and Written Opinion dated Oct. 9, 2014, in PCT International Application No. PCT/JP2013/060003.
(Continued)

*Primary Examiner* — Erik B Crawford
(74) *Attorney, Agent, or Firm* — Birch, Stewart, Kolasch & Birch, LLP

(57) ABSTRACT

A problem to be solved by the present invention is to provide an immunochromatographic test strip and a detection method using immunochromatography avoiding aggregation of colloidal gold conjugates while red blood cells in whole blood are agglutinated and then separated and removed in the case of using polybrene as a blood-agglutinating agent and the colloidal gold conjugates as a detection reagent. To solve the problem, the present inventors reviewed a past reagent configuration itself from a completely different viewpoint rather than selecting type and
(Continued)

amount of polyanions and, as a result of extensive study on each element, the inventors surprisingly found that aggregation of colloidal gold can be suppressed by using a certain buffer solution without using neutralization by polyanions.

5 Claims, 1 Drawing Sheet

(51) Int. Cl.
*G01N 33/543* (2006.01)
*G01N 33/50* (2006.01)
(52) U.S. Cl.
CPC . *G01N 33/54386* (2013.01); *G01N 33/54393* (2013.01); *G01N 33/558* (2013.01); *B01L 2300/0825* (2013.01)

(56) References Cited

U.S. PATENT DOCUMENTS

| 5,064,541 | A | 11/1991 | Jeng et al. |
| 5,262,067 | A | 11/1993 | Wilk et al. |
| 5,725,774 | A | 3/1998 | Neyer |
| 6,673,629 | B2 | 1/2004 | Yoshimura et al. |
| 2001/0006823 | A1 | 7/2001 | Yoshimura et al. |
| 2003/0018357 | A1 | 1/2003 | Luthra et al. |
| 2003/0175846 | A1 | 9/2003 | Parsons et al. |
| 2008/0311680 | A1 | 12/2008 | Chiu |
| 2010/0136566 | A1 | 6/2010 | Mehra et al. |
| 2011/0003320 | A1 | 1/2011 | Ito et al. |
| 2011/0117636 | A1 | 5/2011 | Bae et al. |
| 2013/0011932 | A1 | 1/2013 | Itoh et al. |

FOREIGN PATENT DOCUMENTS

| JP | 60-113154 A | 6/1985 |
| JP | 63-159761 A | 7/1988 |
| JP | 3-205563 A | 9/1991 |
| JP | 5-099918 A | 4/1993 |
| JP | 2002-509254 A | 3/2002 |
| JP | 2007-322310 A | 12/2007 |
| JP | 2010-156576 A | 7/2010 |
| JP | 2011-038903 A | 2/2011 |
| JP | 2011-141252 A | 7/2011 |
| WO | 99/36781 A1 | 7/1999 |

OTHER PUBLICATIONS

International Search Report issued in PCT/JP2013/060003, dated Jun. 25, 2013.
Machine English translation of JP 2007-322310 (Dec. 13, 2007).
Machine English translation of JP 2010-156576 (Jul. 15, 2010).
Machine English translation of JP 2011-38903 (Feb. 24, 2011).
Extended European Search Report dated Oct. 30, 2015, in European Patent Application No. 13768086.4.
Kusano et al., "Immunochromoatographic assay for simple and rapid detection of Satsuma dwarf virus and related viruses using monoclonal antibodies," J. Gen. Plant Pathol. (2007), vol. 73, pp. 66-71.

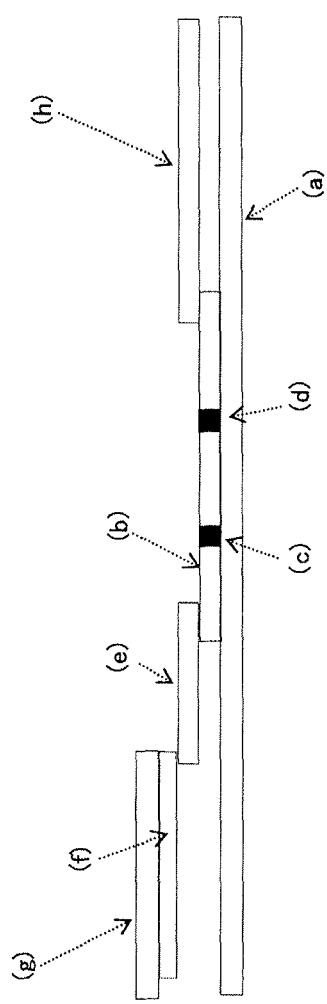

IMMUNOCHROMATOGRAPHIC TEST STRIP AND DETECTION METHOD USING IMMUNOCHROMATOGRAPHY FOR DETECTING TARGET IN RED BLOOD CELL-CONTAINING SAMPLE

PRIORITY CLAIM AND CROSS-REFERENCE

This application is a Divisional of copending application Ser. No. 14/389,180, filed Sep. 29, 2014, which is a U.S. national stage application of International Application No. PCT/JP2013/060003, filed Apr. 1, 2013, which claims the benefit under 35 U.S.C. § 119(a) to Patent Application No. 2012-083165, filed in Japan on Mar. 30, 2012, the contents of which are hereby incorporated by reference in their entirety.

TECHNICAL FIELD

The present invention relates to an immunochromatographic test strip and a detection method using immunochromatography for detecting an object (analyte) in a red blood cell-containing sample. In particular, the present invention relates to a test strip treated with a certain buffer solution to avoid aggregation of colloidal gold conjugates acting as a detection reagent even when a red blood cell-agglutinating agent is used, and a detection method using the buffer solution.

BACKGROUND ART

Clinics and small hospitals recently have increasing needs for "conducting tests and knowing the result during patient consultation" and thus tests are increasingly conducted as point-of-care testing (POCT) instead of conventional outsourced examination. POCT is a collective term for tests generally conducted "near a patient" in an examination room, a hospital ward, etc., and since a doctor can quickly interpret test results to take measures, POCT significantly contributes to the quality of consultation. As POCT as described above becomes popular, devices incorporating lateral flow immunochromatographic test strips etc. are distributed as commodities in the market.

An immunochromatographic test strip enables detection of an object in a sample, without the need of preparation of a reagent at the time of testing, through only a simple operation such as directly dripping a test specimen (sample) such as blood and urine onto the test strip and is very useful for conveniently and quickly analyzing an analyte (detection object) and, therefore, a large number of the test strips are put to practical use for POCT.

The immunochromatographic test strip is generally a membrane made up of a porous body comprising a sample-supply portion, a spreading portion, and a detecting portion and has a structure in which a labeled antibody to an analyte is retained at a spreading start part of the spreading portion in a dissoluble manner such that the labeled antibody can pass through the spreading portion and reach the detecting portion after contact with a sample while an antibody is immobilized at a part of the spreading portion to constitute the detecting portion. When the sample is dripped onto the sample-supply portion, if an analyte is contained in the sample, the analyte in the sample specifically binds to the labeled antibody to form a complex and the complex spreads through the spreading portion in the downstream direction and further binds to the immobilized antibody. Therefore, by detecting a sandwich-type complex of the labeled antibody, the analyte, and the immobilized antibody in the antibody-immobilization part, the analyte can be qualitatively or quantitatively analyzed. An example of a label constituting a detection reagent (conjugate) such as the labeled antibody is colloidal gold particles and a color reaction of the colloidal gold particles enables qualitative detection. The analyte in the sample can also quantitatively be detected based on a degree of coloring.

If a sample is whole blood, red blood cells cannot move in a membrane that is a porous body, and will problematically clog pores of the membrane and obstruct spreading of the sample. Therefore, if whole blood is used as a sample, red blood cells must preliminarily be separated and removed from the whole blood and known methods include a method of removing red blood cells after sedimentation through centrifugation before measurement, and a method of filtrating and removing red blood cells agglutinated by a red blood cell-separating agent before measurement or at the start of measurement.

For example, polybrene is known as a red blood cell-separating agent (Patent Documents 1, 2, and 3).

In Patent Document 1, polybrene is described as an example of a blood-agglutinating agent made of synthetic water-soluble polymer.

In Patent Document 2, a glass-fiber blood cell-separating membrane for chromatography containing polybrene as a red blood cell-agglutinating substance is described. Because passage of blood through a blood cell-separating membrane is associated with hemolysis when polybrene is solely used, a technique is disclosed for coating a blood cell-separating membrane with PVA for avoiding the hemolysis.

Although polybrene is generally known as a blood-agglutinating agent as described above, if polybrene is used for immunochromatography employing a metal conjugate as a detection reagent, polybrene will problematically cause not only aggregation of red blood cells in whole blood but also aggregation of the metal conjugate (Patent Document 3).

Patent Document 3 discloses a technique for preventing such aggregation of a metal conjugate. Briefly, disclosed is an immunochromatography assay device that has a polycation such as polybrene as a blood cell-separating agent bound in the upstream of chromatography carriers and a polyanion for neutralizing the polycation bound in the downstream thereof. It is described that aggregation of a metal conjugate made of selenium can be prevented by this technique since the electric charge of the polycation is neutralized by the polyanion.

CITATION LIST

Patent Literature

Patent Document 1: JP H03-205563 A
Patent Document 2: JP H05-099918 A
Patent Document 3: JP 2002-509254 A

SUMMARY OF INVENTION

Technical Problem

When immunochromatography was practiced using whole blood as a sample and employing polybrene as a blood agglutinating agent and a colloidal gold conjugate as a detection reagent, the present inventors attempted to neutralize positive electric charge of polybrene by adding polyanions so as to prevent aggregation of the colloidal gold conjugate in accordance with the disclosure of Patent Document 3. However, although the red blood cell in the whole blood could be agglutinated and then separated and removed, the aggregation of colloidal gold conjugates could not be prevented. Although the reason is uncertain, this may be attributable to the difference between selenium conjugates of Patent Document 3 and colloidal gold conjugates, and the difference in the type of polyanions, etc.

A problem to be solved by the present invention is to provide an immunochromatographic test strip and a detection method using immunochromatography avoiding aggregation of colloidal gold conjugates while red blood cells in whole blood are agglutinated and then separated and removed in the case of using polybrene as a blood-agglutinating agent and the colloidal gold conjugates as a detection reagent.

Solution to Problem

In order to investigate the method for solving said problem, the present inventors reviewed the configuration of the existing reagent itself from a completely different viewpoint rather than the selection of type or amount of polycations that are causative agents of the problem and, as a result of extensive study on each constituent element, the inventors surprisingly found that there exists a buffer solution which has an ability to suppress aggregation due to polybrene of colloidal gold conjugates and found that aggregation of colloidal gold conjugates can be suppressed by using the buffer solution without relying on the neutralization of polycations by polyanions, and thereby, completing the present invention. In particular, the present invention has the following configuration.

[1] An immunochromatographic test strip comprising the following configuration, (1) a membrane consisting of a porous body equipped with at least a sample-supply portion, a spreading portion, and a detecting portion, wherein a conjugate of an anti-analyte antibody labeled with colloidal gold is retained in a dissoluble manner in a part of the spreading portion, and an antibody is immobilized in the detecting portion which is a part of the spreading portion on the downstream side relative to the conjugate-retaining part, and (2) a buffer solution component for suppressing aggregation of the conjugate due to polybrene, wherein the component is contained at least in a part of from the sample-supply portion to an upstream side of the conjugate-retaining part of the spreading portion so as to be able to contact with polybrene that is a blood-agglutinating agent provided through the sample-supply portion, and wherein the buffer solution component is selected from a group consisting of Bis-Tris, MES, and citric acid.

[2] The test strip of [1], wherein the sample supply portion contains polybrene.

[3] The test strip of [1] or [2], wherein the sample supply portion contains the buffer solution component for suppressing aggregation of the conjugate due to polybrene.

[4] The test strip of any one of [1] to [3] above, wherein a polyanion as a neutralizer neutralizing a cation of polybrene acting as the blood-agglutinating agent is not included.

[5] An immunochromatographic detection method, comprising the steps of:

(A) supplying a sample to a sample-supply portion of a test strip comprising a membrane consisting of a porous body equipped with at least a sample-supply portion, a spreading portion, and a detecting portion, wherein a conjugate comprising a colloidal gold sensitized with an antibody to an object is retained in a dissoluble manner in a part of the spreading portion, and an antibody is immobilized in the detecting portion which is a part of the spreading portion on the downstream side relative to the conjugate-retaining part;

(B) agglutinating a blood-derived component in the sample through contact between polybrene and the sample in the sample-supply portion or in the upstream of the sample-supply portion;

(C) separating and removing aggregates acquired at step (B) from the sample;

(D) bringing a sample component acquired at step (C) after separation and removal of the aggregates into contact with the colloidal gold-containing conjugate, the step being performed in the presence of a buffer solution having ability to suppress aggregation of the conjugate due to polybrene; and (E) detecting a complex of the object in the sample component and the conjugate acquired at the step (D) in the detecting portion, and wherein the buffer solution component is selected from a group consisting of Bis-Tris, MES, and citric acid.

[6] The detection method of [5] above, wherein the sample-supply portion contains polybrene.

[7] The detection method of [5] or [6] above, wherein the sample-supply portion contains the buffer solution component for suppressing aggregation of the conjugate due to polybrene.

[8] The detection method of any one of [5] to [7] above, wherein a polyanion as a neutralizer neutralizing the cation of polybrene acting as the blood-agglutinating agent is not included.

Advantageous Effects of Invention

According to the present invention, in immunochromatography using polybrene as a blood-agglutinating agent and a colloidal gold conjugate as a detection reagent, red blood cells can be agglutinated and then separated and removed from a sample without aggregation of the colloidal gold conjugate by using a buffer solution having ability to suppress aggregation of the colloidal gold conjugate due to polybrene, by which the colloidal gold conjugate can play the original role of the detection reagent and, therefore, an analyte in the sample can accurately be detected and measured. Since addition of a polyanion as a polycation neutralizer is not an essential condition, a reagent configuration can be made extremely simple and, therefore, the present invention advantageously leads to reduction of factors causing unpredictable effect to the immune reaction and to the spread of the analyte on the strip.

BRIEF DESCRIPTION OF DRAWINGS

FIG. 1 is a schematic of structure of an immunochromatographic test strip of the present invention.

DESCRIPTION OF EMBODIMENTS (Immunochromatographic Test Strip)

An immunochromatographic test strip of the present invention is a membrane consisting of a porous body equipped with at least a "sample-supply portion", a "spreading portion", and a "detecting portion" and has a structure in which a labeled antibody to an analyte is retained at a spreading start part of the spreading portion in a dissoluble manner such that the labeled antibody passes through the spreading portion and reaches the detecting portion after contact with a sample while an antibody is immobilized at a part of the spreading portion to constitute the detecting portion.

An example embodying these constituent elements may be a test strip including a sample pad playing a role of a sample-supply portion, a conjugate pad having a labeled antibody to an analyte retained in a dissoluble manner and playing a role of the spreading portion, and an insoluble membrane having an antibody immobilized at a part thereof and playing a role of the spreading portion and the detecting portion. Therefore, a typical immunochromatographic test strip of the present invention has the following configuration:

(1) a sample pad to be supplied with a sample;

(2) a conjugate pad disposed in the downstream of the sample pad and retaining in a dissoluble manner a conjugate in which a first antibody is sensitized on a colloidal gold surface; and (3) an insoluble membrane disposed in the downstream of the conjugate pad and immobilizing a second antibody which binds to a complex of the conjugate and an analyte.

The sample pad, the conjugate pad, and the insoluble membrane may constitute respective different carriers, or two of the elements may constitute one carrier, and may take any form as long as the sample pad, the conjugate pad, and the insoluble membrane are arranged in this order from the upstream toward the downstream.

The immunochromatographic test strip may be a strip further having any one or more of an absorption pad and a 3rd pad disposed and mounted along with the above constituents. The test strip is usually disposed on a solid phase support such as a plastic adhesive sheet. It is obvious that the solid phase support is made of material not hindering the capillary flow of the sample and that an adhesive component is made of material not hindering the capillary flow of the sample. The test strip can be laminated with a polyester film etc., for the purpose of increasing the mechanical strength of the antibody-immobilized membrane and preventing evaporation (drying) of water during an assay.

(Blood-Agglutinating Agent)

A blood-agglutinating agent used in the present invention is preferably polybrene. Polybrene has a chemical name of hexadimethrine bromide and is one of cationic polymers.

In the present invention, polybrene is used for agglutinating red blood cells in whole blood used as a sample. With regard to the manner of using polybrene, polybrene may be added to a diluent which dilutes the sample or may directly be added to the sample and, in other cases, polybrene may be contained in the sample-supply portion (sample pad) of the immunochromatographic strip. In such usage forms, polybrene comes into contact with whole blood and the red blood cells in the whole blood are agglutinated. The aggregates of red blood cells are removed through some kind of filtration, and are removed in the immunochromatographic strip by the sample-supply portion on which a large portion of the aggregates remains when the sample passes through a filter constituting the sample-supply portion. In the present invention, a 3rd pad (blood cell-separating membrane) described later is desirably used together so as to remove the aggregates in the sample-supply portion and more certainly reduce the aggregates supplied to the spreading portion.

The addition amount of polybrene may be any amount capable of agglutinating, separating, and removing red blood cells of the whole blood so that an analyte in the whole blood sample can spread in a desirable manner and, for example, if polybrene is contained in the sample pad, the concentration is preferably equal to or greater than 0.25% and more preferably 0.25 to 2% relative to the fluid volume of the sample to be dropped. In terms of manufacturing of the sample pad, the concentration in the solution impregnated into the pad is preferably equal to or greater than 0.5% and more preferably 0.5 to 4%.

Although polyanions are not included in the present invention unlike Patent Document 3 as a neutralizer for neutralizing the cation of polybrene acting as the blood-agglutinating agent, the presence of polyanions is not excluded as long as the polyanions are normally used as needed within a range not affecting a reaction system without departing from the object of the present invention.

(Certain Buffer Solution)

Although a blood-agglutinating agent (polybrene) is used for the purpose of agglutinating red blood cells in a whole blood sample in the present invention, polybrene has a problem of causing aggregation of not only the red blood cells but also colloidal gold conjugates. In the present invention, a buffer solution must be used so as to avoid such aggregation of the colloidal gold conjugates.

It is essential to use one or more buffer selected from a group consisting of Bis-Tris, MES, and citric acid as the buffer solution used in the present invention. Bis-Tris or MES has an ability to suppress the colloidal gold-conjugate aggregation due to polybrene at pH lower than pKa and citric acid has an ability to suppress the colloidal gold-conjugate aggregation due to polybrene in a wide pH range of pH 4 to 6.5. This is preferable not only in terms of suppression of aggregation due to polybrene but also in terms of buffer solution in immunoassay. Although not bound to any particular theory, all the buffer solution components are effective at pH equal to or lower than pKa and, therefore, the effect is considered as being derived from other than the buffering capacity. It is surprising that a widely used buffer solution component may selectively agglutinate only one of the two kinds of polyanions, i.e., the colloidal gold conjugates and the red blood cells, and may suppress the aggregation of the other in the coexistence state.

The addition amount of these buffer solution components in the buffer solution may be any amount capable of suppressing the aggregation of the colloidal gold conjugates due to polybrene and can experimentally be set. For example, in both a sample pad and a conjugate pad, the addition amount is equal to or greater than 20 mmol/L and preferably 20 to 100 mmol/L in solution impregnated in the pads.

If the concentration of the buffer solution component is unnecessarily high, hemolysis (destruction of red blood cells) may occur, which is not only inconvenient for immunochromatography but also unsuitable for the object of the present invention. Also from this viewpoint, the addition amount is preferably experimentally set.

A usage form of the certain buffer solution of the present invention may be any form capable of suppressing the aggregation of colloidal gold conjugates due to polybrene used as a blood-agglutinating agent, and the certain buffer solution may be impregnated in at least a portion of the immunochromatographic test strip from the sample-supply portion to the conjugate-retaining part of the spreading portion to allow contact with the polybrene component. Therefore, a certain buffer solution may be impregnated in only the sample-supply portion or in the entire part of from the sample-supply portion to the spreading portion. The form of the sample supply portion and/or the conjugate pad impregnated with a buffer solution includes a form in which pads are impregnated with liquid buffer solution as well as a form in which pads are dried after the pads are impregnated with the buffer solution such that the buffer solution component is attached to the pads in a dry state.

The certain buffer solution of the present invention is usable as a sample diluting solution.

Although the certain buffer solution must be used in a certain usage form in the present invention as described above, this does not prevent use of another buffer solution other than those described above for another purpose, or use of the certain buffer solution in another usage form other than those described above. For example, when from the sample-supply portion to a conjugate immobilization part of the spreading portion are impregnated with a certain buffer solution while an antibody-immobilization part of the spreading portion is impregnated with another buffer solution other than those described above, this form is obviously included within the scope of the present invention.

(Colloidal Gold)

Colloidal gold used as a label in the present invention may be any colloidal gold capable of forming a conjugate through sensitization with (immobilization of) an antibody and capable of playing a role of a label in a method of detecting an object (antigen) in a sample through contact with the sample.

With regard to colloidal gold, it is considered that the colloidal gold of the present invention includes colloidal platinum as well as colloidal gold.

The particle diameter of colloidal gold particles is known to significantly affect the measurement sensitivity and, for example, when the colloidal gold particles are retained and used in an immunochromatographic test strip, the particle diameter of colloidal gold particles is preferably 20 to 60 nm, more preferably 30 to 50 nm, and particularly preferably 40 nm. The colloidal gold can be manufactured with a generally known method, for example, by dripping and stirring a trisodium citrate aqueous solution or a triammonium citrate aqueous solution in a heated tetrachloroauric (III) acid aqueous solution. In this description, colloidal gold is also referred to as a colloidal gold particle(s), which has the same meaning.

(Sensitization of Colloidal Gold with Antibody)

The sensitization of colloidal gold with an antibody to an analyte is generally achieved by immobilization such as physical adsorption. In this case, the concentration of antibody is preferably prepared at a concentration of 1 to 5 µg/mL buffer solution. The type and pH of the buffer solution are preferably 2 mmol/L phosphate buffer solution (pH 6.5 to 8) or 2 to 10 mmol/L Tris buffer solution (pH 7 to 9) and more preferably 2 to 10 mmol/L Tris buffer solution (pH 7 to 7.5); however, another buffer solution may be used without any limitation to those listed above. In this description, a "conjugate" refers to colloidal gold as described above sensitized with an antibody to an analyte or with a control antibody (or antigen).

(Blocking)

The conjugate of the present invention can be blocked by a blocking agent in a region of a colloidal gold surface not bound to an antibody.

The blocking agent of the colloidal gold conjugate is generally a component derived from an organism and the component derived from an organism may be any component derived from an organism and having a blocking effect and may be an animal protein or a peptide derived from an animal protein. For example, the component derived from an organism may be bovine serum albumin or BSA, Blocking Peptide Fragment (manufactured by TOYOBO) derived from microorganisms, NEO PROTEIN SAVER (manufactured by TOYOBO) derived from silk protein (hydrolysate of sericin), Starting Block™ (PBS) Blocking Buffer (manufactured by PIERCE), StabilCoat™ (manufactured by SurModics), and casein.

The concentration of a component derived from an organism may appropriately be determined depending on the component to be used. For example, after antibody solution is added to and mixed with colloidal gold solution adjusted to 1 OD/mL, the component derived from an organism is added to the mixture solution to a final concentration within a range of 0.1 to 10% for blocking and is more preferably used within a range of 0.2 to 5%.

Alternatively, both a component not derived from an organism and a component derived from an organism can be mixed and used as a blocking agent of colloidal gold.

(Detection Reagent)

In the present invention, specifically, a "detection reagent" is a solution containing at least a conjugate.

The detection reagent may contain, for example, one or more stabilizers, solubilizers, etc., for the purpose of maintaining the conjugate in a stable state so as to facilitate the specific reaction between the antibody immobilized to the conjugate and the analyte or to make the conjugate dissolved and fluidized promptly and effectively when mixed with the sample. The stabilizers, solubilizers, etc. can include bovine serum albumin (BSA), sucrose, casein, and amino acids, for example.

The detection reagent may contain a known sensitizer such as 2-methacryloyloxyethyl phospholylcholine for the purpose of improvement in detection sensitivity as needed.

The detection reagent may also contain EDTA or EGTA that is a chelating agent of $Ca^{2+}$ ions as needed.

The term "detection" or "measurement" as used herein must be construed in the broadest sense including verification and/or quantification of the presence of the analyte and must not be construed in a limited manner in any sense.

(Diluting Solution)

A diluting solution can be used in the present invention if dilution of a sample is required depending on the concentration of an analyte in the sample. The diluting solution may be a diluting solution of any composition as long as the diluting solution does not significantly inhibit the antigen-antibody reaction or, conversely, does not significantly facilitate the reaction resulting in excessive agglutination causing a defect of spread by capillarity, and does not make the antigen concentration-dependent signal detection of the antigen-antibody reaction impossible.

The diluting solution having such an effect may be, for example, purified water, saline, and a low-concentration buffer solution at pH 6.0 to 10.0, for example, 10 to 20 mmol/L phosphate buffer solution, 10 to 20 mmol/L Tris-HCl buffer solution, and 10 to 20 mmol/L Bis-Tris buffer solution. A surfactant can be added to these diluting solutions so as to control the spread rate of the sample in the strip.

The diluting solution of the present invention can contain polybrene as a blood-agglutinating agent as described above.

The diluting solution of the present invention can also contain a buffer solution component having an ability to suppress the aggregation of colloidal gold conjugates due to polybrene as described above. In this case, the buffer solution of the present invention is used as a diluting solution in place of the buffer solutions described above.

(Sample Pad)

In the present invention, a "sample pad" is a part playing the role of a sample-supply portion receiving a sample and is shaped into a pad to absorb a liquid sample, including any material and form allowing the passage of liquid and the component of the analyte.

The sample pad of the present invention can contain the blood-agglutinating agent as described above. In this case, the blood-agglutinating agent can be contained at least in a part or entirety of the sample pad.

The sample pad of the present invention can contain the certain buffer solution component as described above. In this case, the certain buffer solution component can be contained at least in a part of or entirety of the sample pad. If the sample pad of the present invention contains both the blood-agglutinating agent and the certain buffer solution, the sample pad may contain both at the same part or may contain at respective different parts to avoid coexistence. The sample pad may entirely contain both.

Specific examples of materials suitable for the sample pad include, but not limited to, glass fiber, acrylic fiber, hydrophilic polyethylene material, dry paper, paper pulp, fabric, etc. A glass fiber pad is preferably used. The sample pad may additionally be given a function of a conjugate pad described later. The sample pad may contain a commonly used blocking reagent as needed within a range not affecting the reaction system and not departing from the object of the present invention.

(Conjugate Pad)

In the present invention, a "conjugate pad" refers to a pad acquired by impregnating a material suitable for the conjugate pad described later with a detection reagent specifically reactive with the analyte followed by drying. The conjugate pad has a function of allowing the detection reagent and the analyte to form a complex when the sample passes through the conjugate pad. The conjugate pad may by itself be disposed in contact with an antibody-immobilized membrane. Alternatively, the conjugate pad may be disposed in contact with a sample pad so as to receive the sample which has passed through the sample pad by a capillary flow and then transfer the sample by a capillary flow to another pad (hereinafter also referred to as a "3rd pad") in contact with the surface different from the contact surface for the sample pad. The selection of one or more parts of the sample pad and the conjugate pad and how the selected parts are disposed on the antibody-immobilized membrane may be changed as needed.

The conjugate pad of the present invention can contain the certain buffer solution component as described above. In this case, the certain buffer solution component is contained at least in a part of the upstream side from a part to which the conjugate is immobilized and may be contained in entirety of the conjugated pad.

Materials suitable for the conjugate pad include, but not limited to, paper, a cellulose mixture, nitrocellulose, polyester, acrylonitrile copolymer, glass fiber, and nonwoven fiber such as rayon. A glass fiber pad is preferably used.

The conjugate pad may contain, as needed, a "control reagent" for securing reliability of immunochromatography, for example, an antibody labeled with a label and not reactive with the sample component, or a highly antigenic protein such as KLH (keyhole limpet hemocyanin) labeled with a label. These control reagents are components (substances) having no possibility of being present in the sample and can appropriately be selected.

(3rd Pad)

In the present invention, a 3rd pad can be disposed for the purpose of removing components unnecessary for detection of the analyte out of the components in the sample reacted with the detection reagent so that components necessary for reaction can smoothly spread in the insoluble membrane to which an antibody is immobilized.

For example, blood cells and insoluble blood cell fractures are desirably removed as the components unnecessary for detection. The 3rd pad may also be given an additional effect of preliminarily removing aggregates grown to such a size as to prevent the movement to and the smooth spread in the antibody-immobilized membrane out of aggregates generated by antigen-antibody reactions. The 3rd pad may be made of any material and in any form allowing the passage of liquid and the component to be detected. Specific examples are, but not limited to, glass fiber, acrylic fiber, hydrophilic polyethylene material, dry paper, paper pulp, fabric, etc.

In the present invention, a blood cell-separation membrane is desirably used for certainly separating and removing blood cells not completely removed only by the blood-agglutinating agent and the sample pad described above.

(Immobilization of Antibody to Insoluble Membrane)

In the immunochromatographic reagent of the present invention, an antibody to the analyte can be immobilized to an insoluble membrane with a generally well-known method. For example, in the case of the flow-through format, the antibody is prepared at a predetermined concentration and a certain amount of the solution thereof is applied to the insoluble membrane in a shape of a certain symbol such as dot or "+". In this case, to secure reliability of immunochromatography, a "control line" is generally formed by immobilizing a protein or a compound capable of binding to the conjugate to a position different from the antibody to the analyte. The "control line" may be formed by immobilizing the antibody to the control reagent to a position different from the antibody to the analyte.

In the case of a lateral-flow format, an antibody is prepared at a predetermined concentration and the solution thereof is applied to an insoluble membrane in a line shape by using a device having a mechanism capable of horizontally moving while discharging the solution from a nozzle at a constant rate. In this case, the concentration of the antibody is preferably 0.1 to 5 mg/mL and more preferably 0.5 to 3 mg/mL. An immobilized amount of the antibody on the insoluble membrane can be optimized by adjusting the application amount dripped onto the insoluble membrane in the case of the flow-through format, and can be optimized by adjusting the discharge rate from the nozzle of the device in the case of the lateral-flow format. Particularly in the case of the lateral-flow format, 0.5 to 2 µL/cm is preferable. In the present invention, a "flow-through membrane assay" refers to a format in which the sample liquid etc. spread to perpendicularly pass through the insoluble membrane and a "lateral-flow membrane assay" refers to a format in which the sample liquid etc. spread to move in parallel with the insoluble membrane.

In the present invention, the position of application to the insoluble membrane of an antibody to an analyte may be placed such that the detection reagent spreads from the conjugate pad by capillarity and sequentially passes through the lines to which the respective antibodies are applied in the case of the lateral-flow format. Preferably, the line formed by applying an antibody to an analyte is located upstream while the line formed by applying a control antibody is located downstream thereof. In this case, a sufficient distance is desirably placed between the respective lines such that signals of labels can be detected. In the case of the flow-through format, the position of application of an antibody to an object shall be placed such that signals of labels can be detected.

An antibody solution applied to the insoluble membrane can normally be prepared by using a predetermined buffer solution. The types of the buffer solution may include commonly used buffer solutions such as phosphate buffer solution, Tris buffer solution, and Good's buffer solution. The buffer solution preferably has pH in a range of 6.0 to 9.5 and may appropriately be set depending on the property of the antibody to be used. For example, a buffer solution of pH 7.2 is usable for an anti-H-FABP monoclonal antibody described later. The buffer solution may contain salts such as NaCl, stabilizer and preservative such as sucrose, and antiseptic such as ProClin. The salts include those contained for adjusting ionic strength, such as NaCl, as well as those added at the step of adjusting pH of the buffer solution, such as sodium hydroxide.

After an antibody is immobilized to an insoluble membrane, a blocking can be performed by using a commonly used blocking agent in a solution or in a vapor state to coat a portion other than the antibody-immobilized parts.

In this description, an insoluble membrane having an antibody immobilized as described above is also referred to as an "antibody-immobilized membrane".

(Insoluble Membrane)

In the present invention, an insoluble membrane (hereinafter also simply referred to as a membrane) may be of any material. For example, the materials include, but not limited to, polyethylene, polyethylene terephthalate, nylons, glass, polysaccharide such as cellulose and cellulose derivatives, or ceramics. Specific examples include glass-fiber filter-papers and cellulose filter-papers available from Merck, Toyo Roshi, and Whatman. The pore diameter, structure, etc. of an insoluble membrane can appropriately be selected to control the speed of flow of the immune complex of a colloidal gold-labeled antibody and an object through the membrane. The amount of a labeled antibody binding to an antibody immobilized to the membrane can be adjusted by controlling the speed of flow through the membrane, and therefore, the pore diameter and the structure of the membrane are desirably optimized in consideration of combinations with the other constituent materials of the immunochromatographic test strip of the present invention.

(Absorption Pad)

In the present invention, an absorption pad refers to a liquid-absorbing part absorbing the sample which has moved on and passed through the insoluble membrane to control the spread of the sample. The absorption pad may be disposed at the most downstream portion of the strip configuration in the lateral-flow format, and may be disposed on, for example, the lower portion of the antibody-immobilized membrane in the flow-through format. For example, the absorption pad may be made of filter paper; however, this is not a limitation. Preferably, 740-E of Whatman etc. is used.

(Detection Device)

The immunochromatographic test strip of the present invention can be installed and used in a container (housing) which is appropriate with respect to the size of the strip, the method and position of addition of the sample, the immobilization position of antibody on antibody-immobilized membrane, the signal detection method, etc., and such an installed state is referred to as a "device".

(Others)

In this description, an "insoluble membrane" is also referred to as a "solid phase" and, allowing, or a state of allowing, the insoluble membrane to physically or chemically support antigens or antibodies may be expressed as "immobilization", "immobilized", "solid-phased", "sensitize/sensitization", or "adsorb/adsorption".

(Sample)

In the detection method of the present invention, a "sample" containing an analyte is liquid containing a particulate component having a multiplicity of negative charges on the surface and biological samples can include liquid containing red blood cells and particularly include whole blood, red blood cells separated by centrifugation, etc.

(Analyte)

The analyte of the present invention is a substance present in a biological sample such as blood (whole blood), red blood cells, serum, plasma, urine, saliva, or sputum and is exemplarily illustrated as, for example, inflammation related markers such as CRP (C-reactive protein), IgA, IgG, and IgM, coagulation/fibrinolysis markers such as fibrin degradation products (e.g., D-dimer), soluble fibrin, TAT (thrombin-antithrombin complex), and PIC (plasmin-plasmin inhibitor complex), circulation related markers such as oxidized LDL, BNP (brain natriuretic peptide), and H-FABP (heart-type fatty acid-binding protein), metabolism related markers such as adiponectin, tumor markers such as CEA (carcinoembryonic antigen), AFP ($\alpha$-fetoprotein), CA19-9, CA125, PSA (prostate-specific antigen), infection related markers such as HBV (hepatitis B virus), HCV (hepatitis C virus), Chlamydia trachomatis, and gonococcus, allergen-specific IgE (immunoglobulin E), hormones, and drugs. Among these, preferable objects are D-dimer, CRP, BNP, H-FABP, etc., for which whole blood is in high demand as a sample.

(Antibody Used in the Present Invention)

The antibody to the analyte used in the present invention is not limited in any way by the producing method as long as the antibody is specifically reactive to the analyte, and may be a polyclonal antibody or a monoclonal antibody. A hybridoma producing the antibody can generally be prepared by cell fusion between spleen cells of an animal immunized by using the analyte as an immunogen and myeloma cells from the same species in accordance with the method of Kohler and Milstein (see Nature, Vol. 256, p. 495, 1975).

When monoclonal antibodies are antibodies used in a measurement method of detecting the analyte through formation of so-called sandwich, the relationship between a label-immobilized antibody (first antibody) and an insoluble membrane-immobilized antibody (second antibody) is such that the epitope of the second antibody is different from the first antibody if the epitope of the first antibody is monovalent, and the epitope of the second antibody may be the same as or different from the first antibody if the epitope of the first antibody is multivalent.

In Example 1 described later, an anti-H-FABP monoclonal antibody was used. Although a method of preparing the anti-H-FABP monoclonal antibody used in the present invention is as described in the next section, this is not a limitation of the present invention and a commercially available H-FABP monoclonal antibody may also be used. Examples of the commercially available H-FABP monoclonal antibodies include clones #5B5, #10E1, etc. of HyTest and clones #M79188, #M79189, etc. of Fitzgerald (It is noted that monoclonal antibodies may be denoted by clone names of hybridomas producing the respective antibodies for convenience. The same applies hereinafter).

(Example of Preparation of Anti-H-FABP Monoclonal Antibody)

(1) Preparation of Hybridoma

Human purified H-FABP (manufactured by HyTest) dissolved in PBS was used as an immunogen. This immunogen was mixed and emulsified with complete Freund's adjuvant (manufactured by Wako Pure Chemical Industries) at a ratio of one to one in fluid volume to prepare emulsion having the H-FABP concentration of 0.5 mg/mL, and 100 µL of the emulsion was subcutaneously administered to a six-week-old female BALB/C mouse. Subsequently, 100 µL of emulsion having the H-FABP concentration of 0.2 mg/mL was additionally administered three times in two and a half months, and 100 µL of 0.2 mg/mL human purified H-FABP dissolved in PBS was subcutaneously administered after 10 days from the third additional administration. The spleen, the groin lymph nodes, and the iliac lymph nodes were excised three days later, and the acquired spleen and lymph node cells were mixed with myeloma cells SP2/O—Ag14 at a ratio of six to one for cell fusion in the presence of 50% polyethylene glycol 1540 (manufactured by Wako Pure Chemical Industries). The fused cells were suspended in HAT medium at $2.5\times10^6$/mL as spleen cells and dispensed by 0.2 mL to 96-well culture plate (manufactured by CORNING). The cells were cultured in a 5% $CO_2$ incubator at 37 degrees C. and, after about one week, strains which produce antibodies reactive to H-FABP were selected by using the ELISA method over the culture supernatant of wells with growing hybridomas. Specifically, first, IgG in each of the culture supernatants was solid-phased via goat anti-mouse IgG (Fc) antibodies (manufactured by JACKSON) on a microplate (manufactured by NUNC) and then reacted with H-FABP. Subsequently, reaction was performed with biotin-labeled anti-H-FABP rabbit polyclonal antibodies (manufactured by Proteintech Group) and also with peroxidase-labeled streptavidin (manufactured by PIERCE). A peroxidase substrate solution containing ortho-phenylenediamine (manufactured by Tokyo Chemical Industry) was added for coloring and, after adding 1.5 N sulfuric acid to stop the coloring, measurement was performed by a microplate reader (Abs. 492 nm) to select hybridomas exhibiting high reactivity to H-FABP. Selected hybridomas were cloned with a limiting-dilution method to establish ten types of anti-H-FABP monoclonal antibody-producing hybridomas.

(2) Preparation of Monoclonal Antibody

The hybridomas acquired in (1) were intraperitoneally administered in an amount of $0.2\times10^5$ cells to a 12-week-old female BALB/C mouse preliminarily intraperitoneally injected with 0.5 mL of pristane two weeks before. The ascites was collected after about 14 days, and supernatant was acquired by centrifugation. The supernatant was mixed with the same amount of adsorption buffer solution (3 mol/L NaCl-1.5 mol/L Glycine-NaOH, pH 8.5) and then filtrated. After the filtrate was passed through a protein A column (manufactured by GE Healthcare) equilibrated with the adsorption buffer solution to adsorb antibodies in the filtrate with the column, the antibodies were eluted with 0.1 mol/L citrate buffer solution (pH 3.0) and the anti-H-FABP monoclonal antibodies (Clone #87203 and Clone #87212) were purified.

(Measurement)

A method of quantifying signals derived from colloidal gold may be performed in accordance with a known method and absorbance or reflected light intensity may be measured. Alternatively, the changes in absorbance or reflected light intensity can be extrapolated to the calibration curve of samples with known concentrations to measure the concentration of the object.

(Detection Method Using Immunochromatography)

The detection method using immunochromatography of the present invention is a method comprising at least the following steps of (A) to (E) and is typically a detection method using the immunochromatographic test strip described above:

(A) a step of supplying a sample to a sample-supply portion of a test strip comprising a membrane consisting of a porous body equipped with at least a sample-supply portion, a spreading portion, and a detecting portion, wherein a colloidal-gold-labeled antibody to an analyte (conjugate) is retained in a dissoluble manner in a part of the spreading portion, and an antibody is immobilized in the detecting portion which is a part of the spreading portion on the downstream side relative to the conjugate-retaining part;

(B) a step of agglutinating a blood-derived component in the sample through contact between polybrene and the sample in the sample-supply portion or in the upstream of the sample-supply portion;

(C) a step of separating and removing aggregates acquired at step (B) from the sample;

(D) a step of bringing a sample component acquired at step (C) after separation and removal of the aggregates into contact with a colloidal gold-containing conjugate, the step being performed in the presence of a buffer solution having ability to suppress aggregation of the conjugate due to polybrene; and (E) a step of detecting a complex of the object in the sample component and the conjugate acquired at the step (D) in the detecting portion.

EXAMPLES

The present invention will specifically be described by examples; however, the scope of the present invention is not limited by the examples.

[Example 1] Measurement Using Buffer Solution of the Present Invention (1)

1. Production of Immunochromatographic Device of the Present Invention

1) Preparation of Colloidal Gold-Labeled Anti-H-FABP Monoclonal Antibody (Anti-H-FABP Antibody Conjugate)

(i) Preparation of Colloidal Gold Solution

To 500 mL of purified water heated to 73 degrees C., 1 mL of a 5% (w/v) triammonium citrate aqueous solution was added and then stirred and mixed. Subsequently, 1 mL of a 5% (w/v) tetrachloroauric(III) aqueous solution was added and reacted for 10 minutes with stirring and the reaction solution was then boiled. Subsequently, the reaction solution was cooled in ice water and a solution of colloidal gold with an average particle diameter of 40 nm was prepared. This solution of colloidal gold having an average particle diameter of 40 nm was adjusted to 1 OD/mL with a 20 mmol/L Tris buffer solution (pH 7.0).

(ii) Preparation of Anti-H-FABP Antibody Conjugate

To 20 mL of the 1 OD/mL colloidal gold solution (pH 7.0), 1 mL of the anti-H-FABP monoclonal antibody (Clone #87212) diluted to 46.2 µL/mL by a 2 mmol/L Tris buffer solution (pH 7.0) was added and stirred at room temperature for 10 minutes. To the mixture solution of the colloidal gold and the antibody, 1 mL of a 2 mmol/L Tris buffer solution (pH 7.0) containing a 0.2% (w/v) blocking agent (NEO PROTEIN SAVER: TOYOBO Biochemical, No. NPS-301) was added and stirred at room temperature for 5 minutes. The mixture solution was then centrifuged at 10 degrees C. at 11900×g for 45 minutes. After supernatant was removed, 1 mL of a conjugate-diluting solution (Conjugate Dilution Buffer: SCRIPPS, No. B0221) was added to the acquired sediment to suspend the conjugate to acquire the anti-H-FABP antibody conjugate.

(iii) Preparation of Colloidal Gold-Labeled KLH (KLH Conjugate) for Control Line To 20 mL of the 1 OD/mL colloidal gold solution (pH 6.1), 1 mL of KLH (manufactured by Sigma) diluted to 620 µg/mL by a 2 mmol/L phosphate buffer solution (pH 6.1) was added and stirred at room temperature for 10 minutes. To the mixture solution of the colloidal gold and the KLH, 1 ml of a 10% bovine serum albumin (BSA) aqueous solution was added and stirred at room temperature for 5 minutes. The mixture solution was then centrifuged at 10 degrees C. at 11900×g for 45 minutes. After supernatant was removed, 1 mL of the conjugate-diluting solution was added to the acquired sediment to suspend the conjugate to acquire the KLH conjugate.

2) Production of Conjugate Pad

The anti-H-FABP antibody conjugate and the KLH conjugate prepared in 1), respectively, were mixed to produce conjugate solutions of 16 OD/mL and 4.5 OD/mL with purified water or the following buffer solutions each of the water and buffer solutions containing 2.5% NEO PROTEIN SAVER and 2.4% lactose, and then, a glass fiber pad having a certain volume (Pall Corporation, No. 8964) was impregnated with 1.2 volumes of the conjugate solutions relative to the volume of the pad. The pad was heated and dried at 70 degrees C. for 45 minutes in a dry oven to acquire a conjugate pad. If an additive such as a sensitizer is added as needed, a necessary amount may be added to the conjugate solutions before performing the same operation.

3) Production of Anti-H-FABP Monoclonal Antibody-Immobilized Membrane

The anti-H-FABP monoclonal antibody (Clone #87203) was diluted with a 10 mmol/L phosphate buffer solution (pH 7.2) containing 2.5% sucrose and prepared at 3 mg/mL, and a rabbit anti-KLH polyclonal antibody (manufactured by Bethyl) was diluted with a 10 mmol/L phosphate buffer solution (pH 7.2) containing 2.5% sucrose and prepared to 0.5 mg/mL for the purpose of coloring of the control line. The anti-H-FABP monoclonal antibody was applied onto a nitrocellulose membrane (Merck, HF180, 260 mm×25 mm) at a position inside one end of a short side and the anti-KLH polyclonal antibody was applied at an interval of about 5 mm from the position above by using an immunochromatography dispenser "XYZ3050" (BIO DOT) set to 1 µL/cm in a line shape. The membrane was dried at 70 degrees C. for 45 minutes in a dry oven to acquire an antibody-immobilized membrane.

4) Production of Sample Pad

A glass fiber pad (Lydall) cut to a necessary size as needed was impregnated with the same buffer solution (or purified water) as for the conjugate pad but containing 1% polybrene at 1.15 volumes relative to the volume of the pad and was dried at 70 degrees C. for 45 minutes in a dry oven, and the pad was used as a sample pad.

5) Production of Immunochromatographic Test Strip

To a plastic adhesive sheet (a), the antibody-immobilized membrane (b) was affixed such that antibody-application sites were arranged in the order of the anti-H-FABP antibody (c) on the upstream side of spread and then the anti-KLH antibody (d), and a blood cell-separation film (3rd pad) (e) was further mounted. The conjugate pad (f) produced in 2) was then disposed and mounted and the sample pad (g) produced in 4) was disposed and mounted to overlap the conjugate pad while the absorption pad (h) was disposed and mounted on the end of the other side. The immunochromatographic test strip was produced by cutting into a structure having the constituting elements overlapped with each other as described above. The test strip was installed in a dedicated plastic housing (having a sample-addition window and a detection window not depicted in FIG. 1) at the time of an assay to implement a form of an immunochromatographic test device. FIG. 1 is a schematic of the structure of the immunochromatographic test strip.

2. Test Results

Study on Type of Buffer Solution Applied to Sample Pad

Each immunochromatographic test strip using a sample pad and a conjugate pad impregnated with each of the nine buffer solutions or purified water mentioned above was used for measuring the level of aggregation of the conjugate after contacting with polybrene and completing the spread over a predetermined time. A plasma sample collected and centrifuged in an EDTA-2Na blood-collecting tube (Terumo Corporation) was used as a sample instead of whole blood so as to more clearly reveal the colloidal gold conjugate-aggregation effect of polybrene, and the H-FABP antigen (HyTest) was added. To the sample pad at the window of the test device, 120 µL of the sample was added, and an overlapping portion between the blood cell-separation film (e) and the antibody-immobilized membrane (b) of the test device was uncovered 10 minutes later to measure the reflected light intensity by using the immunochromatography reader ICA-1000 (Hamamatsu Photonics). The measured reflected light intensity was indicated as aggregation sensitivity with "−" indicative of sensitivity equal to or less than 5 mAbs., "±" indicative of sensitivity exceeding 5 mAbs. and equal to or less than 10 mAbs., and "+" indicative of sensitivity exceeding 10 mAbs. The aggregation of colloidal gold particles cannot be confirmed visually at 10 mAbs. or less.

The results are described in Table 1 along with results of Example 2.

[Example 2] Measurement Using Buffer Solution of the Present Invention (2)

A test was conducted for the buffer solution component of Example 1 by using materials different from Example 1.

1. Production of Immunochromatographic Device of the Present Invention (2)

1) Preparation of Colloidal Gold-Labeled Anti-D-Dimer Monoclonal Antibody (Anti-D-Dimer Antibody Conjugate)

(i) Preparation of Colloidal Gold Solution (2)

To 500 mL of purified water heated to 65 degrees C., 0.7 mL of an aqueous solution acquired by dissolving triammonium citrate and trisodium citrate dehydrate both at a ratio of 7% (w/v) was added and then stirred and mixed. Subsequently, 1 mL of a 7% (w/v) tetrachloroauric(III) aqueous solution was added and reacted for 10 minutes with stirring and the reaction solution was then boiled. Subsequently, the reaction solution was cooled in ice water to prepare a solution of colloidal gold with an average particle diameter of 30 nm. The solution of colloidal gold having an average particle diameter of 30 nm was adjusted to 1 OD/mL with a 20 mmol/L Tris buffer solution (pH 7.5).

(ii) Preparation of Anti-D-Dimer Antibody Conjugate

To 20 mL of the 1 OD/mL colloidal gold solution (pH 7.5), 1 mL of the anti-D-Dimer monoclonal antibody (Clone

672102) diluted to 60 μL/mL by a 10 mmol/L Tris buffer solution (pH 7.5) was added and stirred at room temperature for 10 minutes. To the mixture solution of the colloidal gold and the antibody, 1 mL of the blocking agent N102 (manufactured by NOF Corporation) was added and stirred at room temperature for 5 minutes. Subsequently, 2 mL of a 20 mmol/L Tris buffer solution containing 5% (w/v) Blocking Peptide Fragment (manufactured by TOYOBO) was added, further stirred for 5 minutes, and then centrifuged at 10 degrees C. at 11900×g for 45 minutes.

After supernatant was removed, 800 μL of a conjugate-diluting solution was added to the acquired sediment and suspended to acquire the anti-D-Dimer antibody conjugate.

2) Production of Conjugate Pad

The anti-D-Dimer monoclonal antibody-sensitized conjugate prepared in 1) was mixed with purified water or the following buffer solutions each of the water and buffer solutions containing 1.5% Blocking Peptide Fragment and 2.4% lactose solution to produce a conjugate solution of 22 OD/mL, and a glass fiber pad having a certain volume (Pall Corporation, No. 8964) was impregnated with 1.2 volumes of the conjugate solution relative to the volume of the pad. The pad was heated and dried at 70 degrees C. for 45 minutes in a dry oven to acquire a conjugate pad. If an additive such as a sensitizer is added as needed, a necessary amount may be added to the conjugate solution before performing the same operation.

3) Production of Anti-D-Dimer Antibody-Immobilized Membrane

The anti-D-Dimer monoclonal antibody (Clone #DD3B6, manufactured by American Diagnostica) was prepared at 1.5 mg/mL in a 20 mmol/L HEPES buffer solution (pH 8.0) containing 2.5% sucrose, and a fibrin degradation product was diluted and adjusted to 2.5 mg/mL with a 10 mmol/L Tris buffer solution (pH 7.5) containing 2.5% sucrose for the purpose of coloring of the control line. The anti-D-Dimer monoclonal antibody was applied onto a nitrocellulose membrane (Millipore, HF180, 260 mm×25 mm) at a position inside one end of a short side and the fibrin degradation product was applied at an interval of about 5 mm by using an immunochromatography dispenser "XYZ3050" (BIO-DOT) set to 0.8 μL/cm in a line shape. The membrane was dried at 40 degrees C. for 45 minutes in a dry oven to acquire an antibody-immobilized membrane. The fibrin degradation product is prepared from stabilized fibrin by hydrolysis with plasmin. Color develops when the conjugate sensitized with the anti-D-Dimer monoclonal antibody binds to the fibrin degradation product, exhibiting the control line for securing the performance of an immunochromatographic reagent.

4) Production of Sample Pad

The sample pad was produced by the same operation as Example 1.

5) Production of Immunochromatographic Test Strip

The test strip was produced by the same operation as Example 1. It is noted that (c) and (d) were replaced with the anti-D-Dimer antibody and the fibrin degradation product, respectively.

2. Test Results

Study on Type of Buffer Solution Applied to Sample Pad

Each immunochromatographic test strip using a sample pad and a conjugate pad impregnated with each of the nine buffer solutions or purified water was used for measuring the level of aggregation of the conjugate after contacting with polybrene and spreading over a predetermined time. A plasma sample collected and centrifuged in an EDTA-2Na blood-collecting tube (Terumo Corporation) supplemented with the fibrin degradation product was used as a sample instead of whole blood so as to more clearly reveal the colloidal gold conjugate-aggregation effect of polybrene. To the sample pad window of the test device, 120 μL of the sample was added, and an overlapping portion between the blood cell-separation film (e) and the antibody-immobilized membrane (b) of the test device was uncovered 10 minutes later to measure the reflected light intensity by using the immunochromatography reader ICA-1000 (Hamamatsu Photonics). The criterion for judgment is the same as Example 1.

TABLE 1

| Buffer solution | pH | Example 1 Aggregation sensitivity | Judgment | Example 2 Aggregation sensitivity | Judgment |
|---|---|---|---|---|---|
| Bis-Tris | 5.5 | 0.0 | − | 8.3 | ± |
| (pKa: 6.46) | 6.0 | 0.0 | − | 5.2 | ± |
| | 6.5 | 0.0 | − | 169.6 | ++ |
| | 7.0 | 58.3 | + | 295.1 | ++ |
| MES | 5.5 | 0.0 | − | 5.4 | ± |
| (pKa: 6.15) | 7.0 | 4.0 | − | 61.2 | + |
| Citric acid | 4.0 | 0.0 | − | 0.0 | − |
| (pKa: 6.4) | 5.5 | 2.2 | − | 1.5 | − |
| (pKa: 4.76) | 6.5 | 0.0 | − | 4.7 | − |
| (pKa: 2.12) | | | | | |
| Purified water | — | 38.2 | + | 48.8 | + |

When Bis-Tris or MES was used, the effect was confirmed at pH lower than pKa in the studied pH range. For citric acid, the effect was confirmed in the entire studied pH range.

This is common to Examples 1 and 2 and it is confirmed that even when different materials are used, the effect can be exerted on the same condition.

INDUSTRIAL APPLICABILITY

According to the present invention, in an immunochromatography method using polybrene as a blood-agglutinating agent and a colloidal gold conjugate as a detection reagent, red blood cells can be agglutinated and then separated and removed from a sample without aggregation of colloidal gold by using a certain buffer solution and, therefore, an object in a sample can accurately be detected and measured. Since addition of a polyanion as a neutralizer is not an essential condition, a reagent configuration can be made extremely simple and, therefore, the present invention advantageously leads to reduction of factors causing unpredictable effect to the immune reaction and to the spread of the object on the strip.

REFERENCE SIGNS LIST (a) plastic adhesive sheet
(b) antibody-immobilized membrane
(c) anti-H-FABP antibody
(d) anti-KLH antibody
(e) blood cell-separation film (3rd pad)
(f) conjugate pad
(g) sample pad
(h) absorption pad

The invention claimed is:
1. An immunochromatographic test strip comprising:
(1) a membrane comprising a porous body, which comprises a sample-supply portion and a spreading portion, wherein the sample-supply portion is upstream from the spreading portion, wherein the sample-supply portion contains hexadimethrine bromide, wherein a conjugate of an anti-analyte antibody labeled with colloidal gold is retained in a dissoluble manner in a conjugate-retaining part of the spreading portion, and an antibody is immobilized in a detecting part of the spreading portion, which is downstream from the conjugate-retaining part; and (2) a buffer solution component in a dry state, wherein the buffer solution component is contained in the conjugate-retaining part of the spreading portion so as to be able to contact with hexadimethrine bromide provided through the sample-supply portion, and wherein the buffer solution component is selected from a group consisting of Bis-Tris, MES, and citric acid, wherein the test strip does not comprise a polyanion as a neutralizer for neutralizing a cation of the hexadimethrine bromide.

2. The test strip of claim 1, wherein the sample-supply portion contains the buffer solution component.

3. The test strip of claim 1, wherein Bis-Tris and MES are at pH lower than pKa.

4. The test strip of claim 1, wherein the conjugate-retaining part is a conjugate pad.

5. The test strip of claim 4, wherein the sample-supply portion is a sample pad.

* * * * *